United States Patent

Rogers et al.

[11] 4,312,874
[45] Jan. 26, 1982

[54] ANTIBACTERIAL COMPOUNDS, PROCESSES FOR THEIR PREPARATION AND COMPOSITIONS CONTAINING THEM

[75] Inventors: Norman H. Rogers, Horsham; Steven Coulton, Cranleigh, both of England

[73] Assignee: Beecham Group Limited, England

[21] Appl. No.: 204,605

[22] Filed: Nov. 6, 1980

[30] Foreign Application Priority Data

Nov. 10, 1979 [GB] United Kingdom ............... 39015/79

[51] Int. Cl.³ .................... A61K 31/35; A61K 31/44; C07D 309/06
[52] U.S. Cl. .................................. 424/263; 424/283; 260/345.7 R; 260/345.8 R; 260/345.9 R; 542/429; 542/438
[58] Field of Search ............... 260/345.7 R, 345.,8 R, 260/345.9 R; 542/429, 438; 424/283, 263

[56] References Cited

U.S. PATENT DOCUMENTS 4,102,904 7/1978 Lak et al. ..................... 260/345.7 R

*Primary Examiner*—Nicky Chan
*Attorney, Agent, or Firm*—Jacobs & Jacobs

[57] ABSTRACT

A ketone of formula (II):

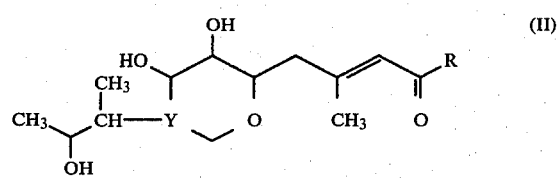

wherein Y represents

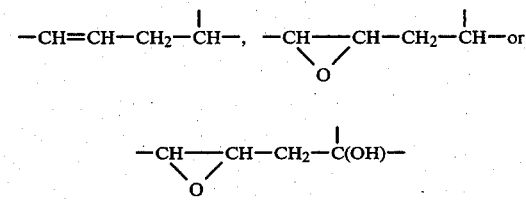

and R represents a $C_{1-10}$ alkyl, $C_{2-10}$ alkenyl, $C_{2-10}$ alkynyl, aryl, aralkyl or cycloalkylalkyl group, optionally substituted with halogen, $C_{1-6}$ alkyl, $C_{1-6}$ alkoxy, hydroxy, carboxy or $C_{1-6}$ alkoxy carbonyl, or represents a 5 or 6 membered heterocyclic group containing a nitrogen, oxygen or sulphur atom, has antibacterial and antimycloplasmal activity and is of value in the treatment of bacterial and mycoplasma-induced human and veterinary diseases.

7 Claims, No Drawings

ANTIBACTERIAL COMPOUNDS, PROCESSES FOR THEIR PREPARATION AND COMPOSITIONS CONTAINING THEM

This invention relates to antibacterial compounds and in particular to a class of ketones which have antibacterial activity against certain Gram-positive and Gram-negative organisms, and also possess anti-mycoplasmal activity. The compounds are therefore of value in the treatment of human and veterinary infections.

The compounds of formula (I) and salts and esters thereof:

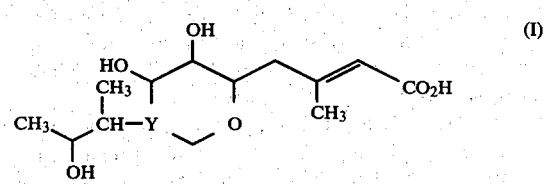

wherein Y represents

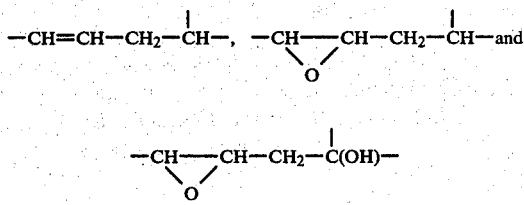

are disclosed in West German Offenlegungsschriften Nos. 2726619, 2726618 and 2848687 and European patent application No. 79300371.6. Compounds of formula (I) having the tri-substituted double bond in the E-configuration are referred to as monic acid C, monic acid A and monic acid B respectively.

The present invention provides a compound of formula (II):

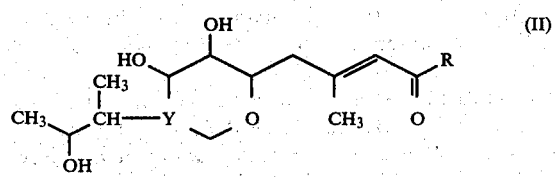

wherein Y is as defined with respect for formula (I); and R represents a $C_{1-10}$ alkyl, $C_{2-10}$ alkenyl, $C_{2-10}$ alkynyl, aryl, aralkyl or cycloalkylalkyl group, optionally substituted with halogen, $C_{1-6}$ alkyl, $C_{1-6}$ alkoxy, hydroxy, carboxy or $C_{1-6}$ alkoxy carbonyl, or represents a 5 or 6 membered heterocyclic group containing nitrogen, oxygen or sulphur atom.

Preferably the compounds of formula (II) are derivatives of monic acid A, ie Y represents

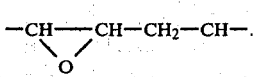

Suitably, R represents a straight or branched chain $C_{1-10}$ alkyl group, preferably a straight chained $C_{1-6}$ alkyl group.

A suitable aryl group for R is phenyl, and a suitable aralkyl group is benzyl. A suitable heterocyclic group is pyridyl.

The compound (II) of this invention incorporates a tri-substituted double bond and may therefore exist in both the E (natural) or Z (or iso) geometrical forms. It is to be understood that both geometrical isomers of the compound of formula (II) are included within the scope of this invention, as well as mixtures of the two isomers. However, because in general the E-isomer of a particular derivative of compound (II) has the greater activity, it is preferable to employ that isomer.

Particular compounds within formula (II) include
1-[3R,4R-dihydroxy-5S-(2S,3S-epoxy-5S-hydroxy-4S-methylhexyl)-tetrahydropyran-2S-yl]-2-methylpent-2E-ene-4-one,
1-[3R,4R-dihydroxy-5S-(2S,3S-epoxy-5S-hydroxy-4S-methylhexyl)-tetrahydropyran-2S-yl]-2-methylhex-2E-en-4-one, and
1-[3R,4R-dihydroxy-5S-(2S,3S-epoxy-5S-hydroxy-4S-methylhexyl)-tetrahydropyran-2S-yl]-2-methyloct-2E-en-4-one.

Compounds of this invention have antibacterial and antimycoplasmal activity, and are therefore of value in the treatment of bacterial and mycoplasma-induced human and veterinary diseases.

The infections against which compounds of this invention are particularly useful include venereal disease. They are also effective in the treatment of respiratory infections such as bacterial bronchitis; and bacterial meningitis, non-specific urethritis and pneumonia. In animals it may be employed for the treatment of mastitis in cattle, for swine dysentery, and for mycoplasma infections in animals such as turkeys, chickens, pigs and cattle.

Some of the human and veterinary diseases either caused by mycoplasma species or in which they play a prominent role, and against which compounds of this invention are effective, are as follows:

| | |
|---|---|
| Avian | |
| M gallisepticum | Chronic respiratory diseases (air-sacculitis) of chickens and turkeys |
| Bovine | |
| M bovis | Mastitis, respiratory disease and arthritis of cattle |
| M dispar | Calf pneumonia |
| Porcine | |
| M suipnuemoniae | Enzootic pneumonia of pigs |
| M hyorhinis | } Arthritis in pigs |
| M hyosynoviae | |
| Human | |
| M pneumoniae | primary atypical pneumonia. |

Compounds of the present invention are particularly useful in the treatment of enzootic pneumonia in animals such as pigs, cattle and sheep, because they also have activity against the bacteria *Bordetella bronchiseptica*, *Pasteurella multocida* and *Haemophilus* spp, which often cause respiratory complications in cases of this disease.

This invention also provides a pharmaceutical or veterinary composition which comprises a compound of formula (II) together with a pharmaceutically or veterinary acceptable carrier or excipient.

The compositions may be formulated for administration by any route, and would depend on the disease being treated. The compositions may be in the form of tablets, capsules, powders, granules, lozenges, liquid or gel preparations, such as oral, topical or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin, hydrogenated edible fats; emulsifying agents, for example lecithin, sorbitan monooleate, or acacia; non aqueous vehicles (which may include edible oils), for example almond oil, fractionated coconut oil, oily esters such glycerine, propylene glycol, or ethyl alchol; preservatives, for example methyl or propyl p-hydroxybenzoate or sorbic acid, and if desired conventional flavouring or colouring agents.

For topical application to the skin compounds of this invention may be made up into a cream, lotion or ointment. Cream or ointment formulations that may be used for compounds of formula (II) are conventional formulations well known in the art, for example, as described in standard text books of pharmaceutics and cosmetics such as Harry's Cosmeticology published by Leonard Hill Books, and the British Pharmacopoeia.

Suppositories will contain conventional suppository bases, eg cocoa-butter or other glyceride.

For parenteral administration, fluid unit dosage forms are prepared utilizing the compound and a sterile vehicle, water being preferred. The compound, depending on the vehicle and concentration used, can either be suspended or dissolved in the vehicle. In preparing solutions the compound can be dissolved in water for injection and filter sterilized before filling into a suitable vial or ampoule and sealing. Advantageously, adjuvants such as a local anaesthetic, preservative and buffering agents can be dissolved in the vehicle. To enhance the stability the composition can be frozen after filling into the vial and water removed under vacuum. The dry lyophilized powder is then sealed in the vial. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compounds.

Veterinary compositions for intramammary treatment of mammary disorders of animals, especially bovine mastitis, will generally contain a suspension of a compound of formula (II) in an oily vehicle.

The compositions may contain from 0.1% to 99% by weight, preferably from 10–60% by weight, of the active material, depending on the method of administration. Where the compositions comprise dosage units, each unit will preferably contain from 50–500 mg, of the active ingredient. The dosage as employed for adult human treatment will preferably range from 100 mg to 3 g, per day, for instance 250 mg to 2 g, per day, depending on the route and frequency of administration.

Alternatively a compound of formula (II) may be administered as part of the total dietary intake. In this case the amount of compound employed may be less than 1% by weight of the diet and in preferably no more than 0.5% by weight. The diet for animals may consist of normal foodstuffs to which the compound may be added or it may be added to a premix.

A suitable method of administration of a compound of formula (II) to animals is to add it to the animals drinking water. In this case a concentration of compound in the drinking water of about 5–500 μg/ml, for example 5–200 μg/ml, is suitable.

The compounds of the present invention may be prepared by methods known for the preparation of α,β-unsaturated ketones. Some of these processes will be more appropriate than others.

A selection of suitable process are outlined below:

Compounds of formula (II) may be prepared by a process which comprises treating an allylic alcohol of formula (III), wherein Y and R are defined with respect to formula (II) and in which the non-allylic hydroxyl groups may be protected, with an oxidising agent which converts allylic alcohols into α,β-unsaturated ketones, and removing any hydroxyl-protecting groups.

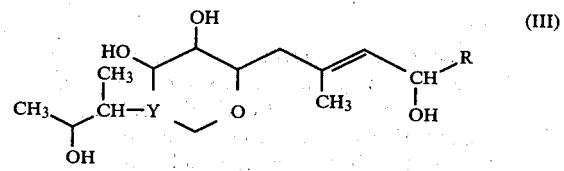

Suitable such oxidising agents include activated manganese dioxide, pyridinium dichromate, and pyridinium chlorochromate.

The allylic alcohol of formula (III) may be prepared by the reaction sequence illustrated in Scheme 1, which comprises the following steps:

(a) reacting an ester of the corresponding monic acid of formula (IV) wherein Y is as defined with respect to formula (I), $R^1$ is an ester forming radical such as alkyl, —$(CH_2)_8CO_2H$ or —$(CH_2)_8CO_2R^x$ wherein $R^x$ is an alkyl group, and any reactive groups may be protected; with a metal hydride reducing agent, such as di-isobutyl aluminium hydride, sodium di-(2-methoxyethoxy)-dihydroaluminate or lithium triethyl borohydride.

(b) oxidising the generated allylic alcohol (V) with an oxidising agent such as activated manganese dioxide, pyridinium dichromate or pyridinium chlorochromate. A preferred oxidising agent is activated manganese dioxide.

(c) reaction with an organometallic reagent; such as a Grignard reagent of formula R MgX, wherein R is defined with respect to formula (II) and X represents chlorine, bromine; or iodine or a lithium reagent of formula RLi wherein R is defined with respect to formula (II). The reaction with a Grignard reagent may optionally be carried out in the presence of copper (I) iodide as catalyst.

SCHEME 1

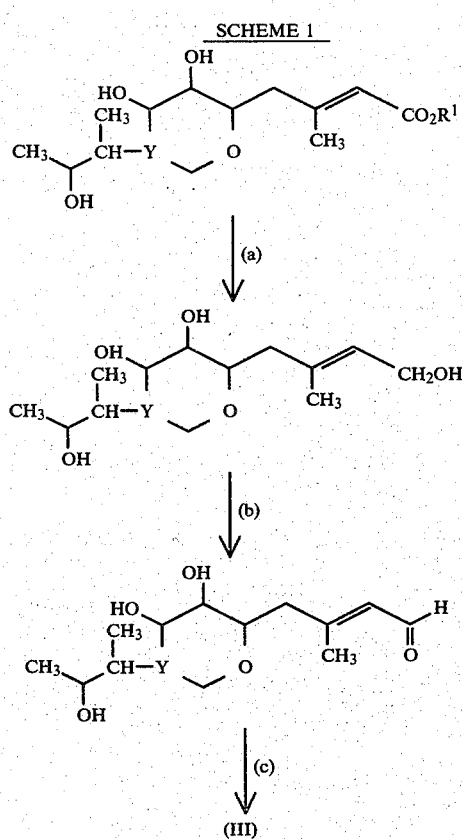

The steps using organometallic reagents, ie, steps (a) and (c) are conveniently carried out in an ethereal or hydrocarbon solvent, the choice of which is dependent upon the specific requirements of the organometallic reagent; preferably the Grignard reagent in step (c) is generated and used in diethyl ether. These reactions are generally carried out in an inert atmosphere such as argon, and at ambient temperature or below. The period for which the reaction is allowed to proceed depends upon the particular starting material employed. The course of the reaction may be followed by conventional methods such as thin layer chromatography and terminated when an optimum quantity of product is present in the reaction mixture.

The oxidation reactions step (b), and the oxidation of compound (III) are conveniently carried out in polar organic solvents, the choice of which is not critical to the success of the reaction provided that the organic reagent is soluble to some extent and the solvent is substantially inert to the reagents and product.

Prior to the above process of this invention, it may be desirable to protect the hydroxyl groups in compound (IV). Although the reactions of the compounds (IV), (V), (VI) and (III) are possible without hydroxyl protection, in general higher yields of the product (II) are formed if the hydroxyl groups are protected. Such protecting groups must be removable under suitably mild conditions and suitable protecting groups are described below.

The intermediate of formula (VI) may also be prepared by a process which comprises either;

(i) reaction of a compound of formula (I), i.e. monic acid, wherein any reactive groups may be protected, with carbonyldi-imidazole to give the imidazolyl derivative thereof, followed by reduction of the derivative with a metal hydride reducing agent. Suitable reducing agents include sodium-di-(2-methoxyethoxy)-dihydroaluminate and lithium aluminium hydride or (ii) reaction of a compound of formula (IV) or a suitably protected derivative thereof, wherein Y and $R^1$ are as defined hereinbefore, with a metal hydride reducing agent, such as sodium di-(2-methoxyethoxy)-dihydroaluminate or (iii) reaction of a compound of formula (VII) or a suitably protected derivative thereof:

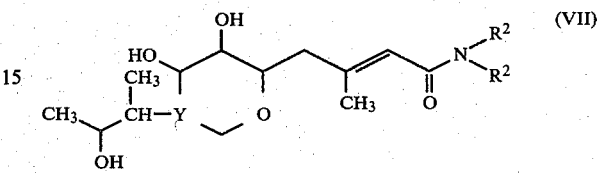

wherein Y is as defined with respect to formula (I) and the groups $R^2$ may be the same or different and each represents hydrogen or an alkyl group, with a metal hydride reducing agent, such as sodium di-(2-methoxyethoxy)-dihydroaluminate.

A suitable method of preparing compounds in formula (II) wherein R is methyl comprises reaction of a suitably protected derivative of a compound of formula (VIII):

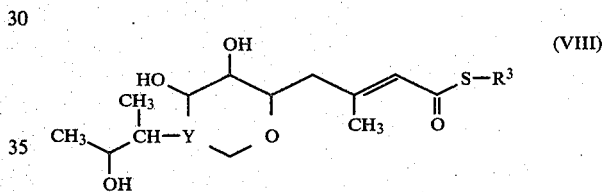

wherein Y is defined with respect to formula (I), $R^3$ represents $C_{1-20}$ alkyl, aryl and aralkyl, with lithium dimethyl cuprate in dry ethereal solvent.

Other methods suitable for preparing $\alpha\beta$-unsaturated ketones include:

(a) reaction of an $\alpha\beta$-unsaturated acid or its imidazolyl derivative with a Grignard reagent, Chem. Ber., 1962, 95, 1284;

(b) reaction of an $\alpha\beta$-unsaturated ester with trimethylsilylmethyl lithium followed by elimination of the trimethylsilyl group, M. Demuth, Helvetica, 1978, 61, 3136; and (c) reaction of a ketone with a terminal alkyne followed by reaction with tris(triphenylsilyloxy) vanadate and triphenylsilanol, H. Pauling, Helvetica, 1976, 59, 1233, G. L. Olson, Helvetica, 1976, 59, 567.

Suitable ketones include compounds of formula (IX):

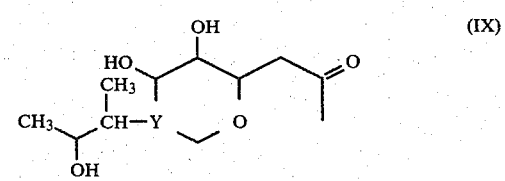

wherein Y is defined with respect to formula (I).

Compounds of formula (II) wherein Y represents

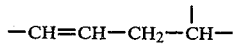

may also be prepared from compounds of formula (II) wherein Y represents

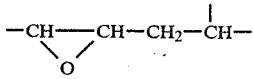

by reaction with a reagent which converts as epoxide to an olefin. Suitable methods of performing this process are disclosed in our published European patent application No. 0003069.

As indicated hereinbefore prior to any of the above processes it may be desirable to protect the hydroxyl groups in the starting material. Such protecting groups must be removable under suitably mild conditions and suitable groups include trimethyl silyl groups produced from a silylating agent such as N,O-bis(trimethylsilylacetamide).

A preferred process for the preparation of compounds of formula (II) comprises treating a mixed anhydride of formula (X):

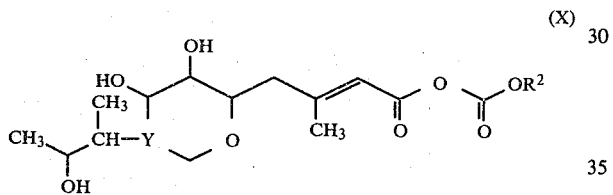

in which $R^2$ is a $C_{1-6}$ alkyl group and Y is as defined with respect to formula (II) whose hydroxyl groups are optionally protected preferably by trimethylsilyl groups, with a compound of formula (XI):

wherein R is as defined with respect to formula (II). The hydroxyl protecting groups, if present, may be subsequently removed under suitably mild conditions. The above reaction is particularly suitable for the case where R is a $C_{1-6}$ alkyl group. In this case the compound RMnCl may conveniently be prepared under an atmosphere of argon or nitrogen by addition of an alkyl lithium to a solution of manganous chloride and lithium chloride in dry THF, or a suspension of anhydrous manganous chloride in dry THF. An excess of RMnCl is preferably employed. Alternatively, a Grignard reagent may be used in place of the alkyl lithium to generate RMnCl. Other organomanganous reagents which may be used in place of RMnCl are:

(i) $R_3MnLi$ or $R_3MnMgX$ in THF wherein X is a halogen atom [Synthetic Communications, 1979, 9, 639]

(ii) RMnI in ether [Synthetic Communications 1979, 9, 639]

(iii) RMnBr in ether [Tet. Letters, 1976, 3155]

As in the case of RMnCl, the above organomanganous reagents may be prepared in situ when required.

The following Examples illustrate the preparation of a number of compounds of the invention.

EXAMPLE 1

1-[3R,4R-Dihydroxy-5S-(2S,3S-epoxy-5S-hydroxy-4S-methylhexyl)-2,3,5,6-tetrahydropyran-2-S-yl]-2-methylpent-2E-en-4-one The ethanethiol ester of monic acid A (0.780 gm; 2 mM) was dissolved in dry acetonitrile (25 ml) and stirred at room temperature for one hour with N,O-bis-(trimethylsilyl)-acetamide (4 ml). The solvent was then removed at reduced pressure and 40° C.

Cuprous iodide (1.14 gm; 6 mM) was suspended in dry diethyl ether (50 ml) under an argon atmosphere and cooled to 0° C. Methyl lithium (2 M solution in diethyl ether; 6 ml; 12 mM) was then added and the suspension stirred at 0° C. for 30 minutes. The tristrimethylsilyl ether of the ethanethiol ester of monic acid A was then dissolved in dry tetrahydrofuran (50 ml) and added to the reaction mixture, which was then, stirred at 0° C. for two hours and room temperature for sixteen hours, under an argon atmosphere. The reaction was quenched by the dropwise addition of a saturated solution of ammonium chloride (10 ml) and the product extracted with ethyl acetate. The organic layer was washed with water, saturated sodium chloride solution and dried over anhydrous magnesium sulphate. After filtration, the solvent was removed at reduced pressure and the residue dissolved in 1,4-dioxan/water (4:1; 10 ml). Two drops of 1 Normal hydrochloric acid were added and the solution stirred for three minutes. Excess sodium bicarbonate solution was then added and the product extracted with ethyl acetate. The organic layer was washed with water, saturated sodium chloride solution and dried over anhydrous magnesium sulphate. Filtration and removal of the solvent at reduced pressure gave the crude ketone as an oil. This oil was purified by column chromatography over silica gel (Type 60; 20 gm). Elution with 5% methanol/chloroform afforded the pure α,β-unsaturated methyl ketone as a colourless oil. This oil crystallised on scratching with diethyl ether to yield a white solid (0.310 gm; 45%), M.pt. 104°–106° C. (ether/hexane), (Found: C, 62.9; H, 8.7. $C_{18}H_{30}O_6$ requires: C, 63.1; H, 8.8%), λmax (EtOH) 239 nm (єm 10,500); νmax (CHBr$_3$) 3410, 1682, 1618 cm$^{-1}$; δH (CDCl$_3$) 6.15 (1H, s, CH=C); 2.16 (6H, s, COCH$_3$+CH$_3$-15); 1.21 (3H, d, J=6.0 Hz, CH$_3$-14); 0.93 (3 H, d, J=6.0 Hz; CH$_3$-17); δ$_C$ (CDCl$_3$) 199.3 (s), 156.1 (s) 125.5 (d), 75.0 (d), 70.9 (d), 70.3 (d), 68.9 (d), 65.5 (t), 61.1 (d), 55.6 (d), 43.2 and 42.7 (d+t), 39.7 (d), 31.7 (q+t), 20.7 (q), 19.6 (q), 12.5 (q), m/e (ammonia C.I.) 360 (100%, M+NH$_4^+$), 343 (15, M+H$^+$), 325 (20), 307 (5), m/e (E.I.) 342.2061 (0.5, M$^+$, $C_{18}H_{30}O_6$ requires 342.2079), 227 (20), 43 (100%).

EXAMPLE 2

(a)

4-[3,4-Dihydroxy-5-(2,3-epoxy-5-hydroxy-4-methylhexyl)tetrahydropyran-2-yl]-3-methylbut-2E-en-1-ol Methyl pseudomonate A (0.2 g, 0.039 mM) was dissolved in dry tetrahydrofuran (50 ml) and cooled to 0° C. while stirring under an argon atmosphere. Diisobutyl-aluminium hydride (25% solution in toluene; 1.5 ml, 2.64 mM) was slowly added and the reaction mixture allowed to reach room temperature. Stirring was then continued for a further 48 hours, under an argon atmosphere. The reaction was quenched by water and then filtered. The residual solid was washed well with methanol and the filtrate evaporated at reduced pressure to yield an oil. This oil was purified by preparative thin layer chromatography using two 20×20×0.2 cm silica plates, eluting with 12% methanol/chloroform. The allylic alcohol was obtained as a colourless oil (0.09 g, 70%), $\nu_{max}$(CHBr$_3$) 3400, 1665 cm$^{-1}$, $\delta$H (CDCl$_3$) 5.48 (1 H, broad t, C=CH); 4.13 (2H, d, CH$_2$OH); 1.72 (3H, s, CH$_3$-15); 1.21 (3 H, d, J=6.5 Hz, CH$_3$-14); 0.92 (3H, d, J=7.0 Hz, CH$_3$-17), $\delta_C$ (CD$_3$OD) 136.7 (s), 126.9 (d), 76.5 (d), 71.5 (d), 70.6 (d), 70.1 (d), 66.1 (t), 61.3 (d), 59.3 (t), 56.8 (d), 43.5 (d), 42.3 (t), 41.1 (d), 32.8 (t), 20.3 (q), 16.6 (q), 12.2 (q). m/e 330 (M+), 312, 267, 244, 227, 141 (100%, 129, 111, 99.

(b) 4-[3R,4R-Dihydroxy-5S-(2S,3S-epoxy-5S-hydroxy-4S-methylhexyl)tetrahydropyran-2S-yl]-3-methylbut-2E-enal The allylic alcohol (0.300 g) was dissolved in acetone (12 ml) and stirred for 30 minutes at room temperature with freshly prepared 'Attenburrow' activated manganese dioxide (2.5 g), when t.l.c. (9:1 CHCl$_3$/CH$_3$OH) indicated complete reaction. The suspension was then filtered through celite, washing thoroughly with acetone. The filtrate was then evaporated at reduced pressure to yield the crude α,β-unsaturated aldehyde as a pale yellow oil (0.200 g). The produce was purified by preparative t.l.c. on two 20×20×0.2 cm silica plates, eluting with 12% methanol/chloroform. The major band gave the pure α,β-unsaturated aldehyde as a colourless oil (0.137 g; 46%; λ$_{max}$ (EtOH) 241 nm (εm 12,700); $\nu_{max}$(CHBr$_3$) 3425, 1665 cm$^{-1}$; $\delta_H$(CDCl$_3$) 9.9

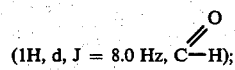
(1H, d, J = 8.0 Hz, C—H);

5.92 (1H, d, J=8.0 Hz, CH=C); 2.20 (3H, s, CH$_3$-15); 1.17 (3H, d, J=6.0 Hz, CH$_3$-14); 0.92 (3H, d, J=7.0 Hz, CH$_3$-17); $\delta_C$ (CDCl$_3$) 191.7 (d), 162.5 (s), 128.8 (dd, J=155 Hz and 17 Hz), 74.9 (d), 71.0 (d), 70.3 (d), 68.8 (d), 65.5 (t), 61.1 (d), 55.6 (d), 42.7 (d+t), 39.7 (d), 31.7 (t), 20.7 (q), 18.2 (q), 12.6 (q); m/e (E.I.) 310.1781 (1%, M+—H$_2$O, C$_{17}$H$_{26}$O$_5$ requires 310.1783), 227 (15%).

(c) 1-[3R,4R-Dihydroxy-5S-(2S,3S-epoxy-5S-hydroxy-4S-methylhexyl)tetrahydropyran-2S-yl]-2-methylhex-2E-en-4R,S-ol 4-[3R,4R-Dihydroxy-5S-(2S,3S-epoxy-5S-hydroxy-4S-methylhexyl)tetrahydropyran-2S-yl]-3-methylbut-2E-enal (0.190 gm; 0.58 mM) was dissolved in dry acetonitrile (20 ml) and stirred at room temperature for one hour with N,O-bistrimethylyacetamide (1 ml). The solvent was then removed at reduced pressure and 40° C.

Ethyl magnesium bromide (2 M solution in diethyl ether; 0.9 ml; 1.8 mM) was added to a suspension of copper I iodide (0.030 gm; 0.16 mM) in dry tetrahydrofuran (50 ml) at −78° C. under an argon atmosphere. The suspension was stirred at this temperature for a further fifteen minutes.

The protected α,β-unsaturated aldehyde was added as a solution in dry tetrahydrofuran (10 ml) to the reaction mixture which was then stirred at −78° C. for fifteen minutes, 0° C. for one hour and room temperature for sixteen hours, under an argon atmosphere. The reaction was quenched by the addition of excess saturated ammonium chloride solution and the product extracted with ethyl acetate. The organic layer was washed with sodium bicarbonate solution, saturated brine, dried over anhydrous magnesium sulphate and the solvent removed at reduced pressure. The residue was dissolved in 1,4-dioxan/water (4:1; 10 ml). Two drops of 1 N hydrochloric acid were added and the solution stirred at room temperature for three minutes. Excess sodium bicarbonate solution was added and the solution layered with ethyl acetate. The aqueous layer was saturated with sodium chloride and the organic layer separated, washed with water, brine and dried over anhydrous magnesium sulphate. Removal of the solvent at reduced pressure yielded the crude product as a colourless oil, which was purified by silica gel column chromatography (Type 60; 4 gm), eluting with 5% methanol/chloroform. The pure secondary allylic alcohol was obtained as a colourless oil (0.180 gm; 87%), $\nu_{max}$(CHBr$_3$) 3400, 1622 cm$^{-1}$, $\delta_H$(CDCl$_3$) 5.25 (1H, d, CH=C); 4.27 (1H, m, C=CCH—CH); 1.72 (3H, s, CH$_3$-15); 1.45 (2H, m, CH$_2$CH$_3$); 1.21 (3H, d, CH$_3$-14); 0.9 (6H, d+t, CH$_3$-17 and CH$_2$CH$_3$), $\delta_C$ (CDCl$_3$) 135.5+135.1, 130.4+130.0, 75.5, 71.0, 70.5, 69.8, 69.3+68.9, 65.4, 61.2, 55.7, 42.7, 41.7+41.2, 39.3, 31.9, 30.5, 20.8, 17.2, 12.6, 9.8 m/e 358.2358 (1%, M+, C$_{19}$H$_{34}$O$_6$ requires 358.2361), 340 (8%), 96 (100%).

(d) 1-[3R,4R-Dihydroxy-5S-(2S,3S-epoxy-5-S-hydroxy-4S-methylhexyl)tetrahydropyran-2S-yl]-2-methylhex-2E-en-4-one 1-[3R,4R-Dihydroxy-5S-(2S,3S-epoxy-5S-hydroxy-4S-methylhexyl)tetrahydropyran-2S-yl]-2-methylhex-2E-en-4R, S-ol (0.089 gm; 0.25 mM) was dissolved in dry dichloromethane (10 ml) and stirred at room temperature for one hour with pyridinium chlorochromate (0.080 gm; 0.37 mM) and powdered sodium acetate (0.050 gm). Diethyl ether was added and the suspension filtered. The filtrate was evaporated to dryness and partitioned between ethyl acetate and sodium bicarbonate solution. The organic layer was washed with saturated brine and dried over anhydrous magnesium sulphate. Removal of the solvent at reduced pressure gave the crude ketone as a black oil (0.070 gm). The product was purified by silica gel column chromatography (Type 60; 1.5 gm). Elution with 5% methanol/chloroform afforded the pure α,β-unsaturated ethyl ketone as a pale yellow oil (0.010 gm; 11%), λmax (EtOH) 238 nm (εm 6,540), $\nu$max (CHCl$_3$) 3430, 1682 and 1620 cm$^{-1}$, $\delta_H$ (CDCl$_3$) 6.11 (1H, s, CH=C); 2.43 (2H, q, CH$_2$CH$_3$); 2.16 (3H, s, CH$_3$-15); 1.20 (3H, d, J=7.0 Hz, CH$_3$-14); 0.95 (6H, d+t, CH$_2$CH$_3$+CH$_3$-17), m/e 356.2233 (1%; M+; C$_{19}$H$_{32}$O$_6$ reqires 356.2268), 338 (2%), 320 (2%), 244 (20%), 227 (40%), 57 (100%).

EXAMPLE 3

1-[3R,4R-Dihydroxy-5S-(2S,3S-epoxy-5S-hydroxy-4S-methylhexyl)tetrahydropyran-2S-yl]-2-methyloct-2E-en-4R,S-ol 4-[3R,4R-Dihydroxy-5S-(2S,3S-epoxy-5S-hydroxy-4S-methylhexyl)tetrahydropyran-2S-yl]-3-methylbut-2E-enal (0.150 gm; 0.46 mM) was dissolved in dry acetonitrile (20 ml) and stirred at room temperature for one hour with N,O-bistrimethylsilylacetamide (1 ml). The solvent was then removed under reduced pressure at 40° C.

n-Butyl magnesium bromide (2 M solution in diethyl ether; 0.8 ml; 1.6 mM) was added to a suspension of copper I iodide (0.030 gm; 0.16 mM) in dry tetrahydrofuran (50 ml) at −78° C. under an argon atmosphere. The suspension was stirred at this temperature for a further fifteen minutes.

The protected α,β-unsaturated aldehyde was then added as a solution in dry tetrahydrofuran (10 ml) to the reaction mixture, which was then stirred at −78° C. for fifteen minutes, 0° C. for one hour and room temperature for sixteen hours, under an argon atmosphere. The reaction was quenched by the addition of excess saturated ammonium chloride solution and the product extracted with ethyl acetate. The organic layer was washed with sodium bicarbonate solution, saturated brine, dried over anhydrous magnesium sulphate and the solvent was then removed at reduced pressure. The residue was dissolved in 1,4-dioxan/water (4:1, 10 ml). Two drops of 1 N hydrochloric acid were added and the solution stirred at room temperature for three minutes. Excess sodium bicarbonate solution was added and the solution layered with ethyl acetate. The aqueous layer was saturated with sodium chloride and the organic layer separated, washed with water, brine and dried over anhydrous magnesium sulphate. Removal of the solvent at reduced pressure yielded the crude product as a pale yellow oil (0.140 gm) which was purified by silica gel column chromatography (Type 60; 10 gm), eluting with 5% methanol/chloroform. The pure alcohol was obtained as a colourless oil (0.076 gm; 43%), $\nu_{max}$(CHBr$_3$) 3400, 1640 cm$^{-1}$; $\delta_H$(CDCl$_3$) 5.26 (1H, d, C=CH), 4.32 (1H, broad t, C=CH=CH), 1.72 (3H, s, CH$_3$-15), 1.30 (m, CH$_2$ protons), 1.22 (3H, d, CH$_3$-14), 0.93 (6H, d+t, CH$_3$-17+(CH$_2$)$_3$—CH$_3$); $\delta_C$ (CDCl$_3$) 135.5 (s)+135.0 (s), 131.0 (d)+130.6 (d), 75.6 (d), 71.3 (d), 70.7 (d), 69.6 (d)+69.1 (d), 68.7 (d), 65.6 (t), 61.4 (d), 55.9 (d), 42.9 (d), 41.9 (t)+41.3 (t), 39.5 (d) 39.3 (d), 37.6 (t), 32.1 (t), 27.8 (t), 22.9 (t), 21.1 (q), 17.4 (q), 14.3 (q), 12.8 (q); m/e (NH$_3$ C.I.) 404 (8%, M+NH$_4$), 386 (10%, M—H$_2$O+NH$_4$), 369 (65%, M—H$_2$O+H), 351 (85%, M—2H$_2$O+H).

(b)
1-[3R,4R-Dihydroxy-5S-(2S,3S-epoxy-5S-hydroxy-4S-methylhexyl)tetrahydropyran-2S-yl]-2-methyloct-2E-en-4-one 4-[3R,4R-Dihydroxy-5S-(2S,3S-epoxy-5S-hydroxy-4S-methylhexyl)tetrahydropyran-2S-yl]but-2E-enal (0.200 gm; 0.61 mM) was dissolved in dry acetonitrile (20 ml) and stirred at room temperature for one hour with N,O-bistrimethylsilylacetamide (1 ml). The solvent was then removed under reduced pressure at 40° C.

n-Butyl magnesium bromide (2 M solution in diethyl ether; 1 ml; 2 mM) was added to a suspension of copper I iodide (0.038 gm; 0.2 mM) in dry tetrahydrofuran (50 ml) at −78° C. under an aron atmosphere. The suspension was stirred at this temperature for a further fifteen minutes and then the protected α,β-unsaturated aldehyde was added as a solution in dry tetrahydrofuran (10 ml). The reaction mixture was stirred at −78° C. for fifteen minutes, 0° C. for one hour and room temperature for three days, under an argon atmosphere. The reaction was quenched by the addition of excess saturated ammonium chloride solution. The resulting solution was extracted with ethyl acetate and the organic layer washed with water, saturated sodium chloride solution and dried over anhydrous magnesium sulphate. Removal of the solvent at reduced pressure yielded a pale yellow oil, which was dissolved in dry dichloromethane (20 ml). Powdered sodium acetate (0.110 gm) was added to the solution; followed by pyridinium chlorochromate (0.263 gm; 1.22 mM). The suspension was stirred at room temperature for one hour and then triturated with dry diethyl ether (50 ml). The resulting black suspension was filtered through a pad of florasil, washing several times with ether. The filtrate was evaporated to dryness at reduced pressure and the residual oil partitioned between ethyl acetate and water. The organic layer was washed with sodium bicarbonate solution, sodium chloride solution, dried over magnesium sulphate and the solvent removed at reduced pressure to afford a pale yellow oil, which was redissolved in 1,4-dioxan/water (4:1; 5 ml). 1 N Hydrochloric acid (two drops) was added and the solution shaken at room temperature for three minutes. Excess sodium bicarbonate solution was added, the aqueous solution saturated with sodium chloride and the product extracted with ethyl acetate. The organic layer was washed with sodium chloride solution, dried over magnesium sulphate and the solvent evaporated at reduced pressure to yield the crude α,β-unsaturated n-butyl ketone as a yellow oil (0.110 gm). The product was purified by silica gel column chromatography (Type 60; 3 gm). Elution with 2% methanol/chloroform afforded the pure ketone as a colourless oil (0.027 gm, 12%), λ max (EtOH) 239 nm (εm 9.800); $\nu$ max (CHBr$_3$) 3400, 1680, 1615 cm$^{-1}$; δ H (CDCl$_3$) 6.12 (1H, s, CH=CC), 2.42 (t, COCH$_2$), 2.15 (3H, s, CH$_3$-15), 1.5–1.1 (10H, m, +d, CH$_3$-14+methylene protons), 0.93 (6 H, broad d, CH$_3$-17+butyl-CH$_3$); $\delta_C$(CDCl$_3$), 201.7, 155.0, 125.2, 75.1, 71.3, 70.4, 69.0, 65.5, 61.3, 55.6, 44.2, 43.2, 42.8, 39.6, 31.7, 26.4, 22.4, 20.8, 19.6, 13.9, 12.7; m/e 384.2487 (2%, M+, C$_{21}$H$_{36}$O$_6$ requires 384.2464), 366 (2%), 348 (3%), 244 (30%), 227 (55%), 209 (20%), 152 (65%), 85 (100%).

1-[3R,4R-Dihydroxy-5S-(2S,3S-epoxy-5S-hydroxy-4S-methylhexyl)tetrahydropyran-2S-yl]-2-methyloct-2E-en-4-one 1-[3R,4R-Dihydroxy-5S-(2S,3S-epoxy-5S-hydroxy-4S-methylhexyl)tetrahydropyran-2S-yl]-2-methyloct-2E-en-4R,S-ol (0.005 gm; 0.013 mM) was dissolved in dry dichloromethane (2 ml) and stirred at room temperature for one hour with pyridinium chlorochromate (0.005 gm; 0.023 mM) and powdered sodium acetate (0.005 gm). Diethyl ether was added and the suspension filtered. The filtrate was evaporated to dryness and partitioned between ethyl acetate and sodium bicarbonate solution. The organic layer was washed with saturated brine and dried over anhydrous magnesium sulphate. Removal of the solvent at reduced pressure gave the crude ketone chromatographically identical to material obtained in example 3b.

EXAMPLE 4

1-[3,4-Dihydroxy-5-(2,3-epoxy-5-hydroxy-4-methylhexyl)tetrahydropyran-2-yl]-2-methyloct-2Z-en-4-one The methanethiol ester of monic acid A (0.374 g, 1 mM;) was dissolved in dry acetonitrile (25 ml) and stirred at room temperature for 1 hour with N,O-bis-(trimethylhexyl)tetrahydropyran-2-yl]-2-methyloct-2Z-en-4-one The methanethiol ester of monic acid A (0.374 g. 1 mM;) was dissolved in dry acetonitrile (25 ml) and stirred at room temperature for 1 hour with N,O-bis- (trimethylsilyl)-acetamide (2 ml). The solvent was then removed at reduced pressure and 40° C.

Cuprous iodide (0.570 g; 3 mM) was suspended in dry ether (25 ml) under an argon atmosphere and cooled to 0° C. n-Butyl lithium (2 M solution in hexane; 3 ml; 6 mM) was then added and the suspension stirred at 0° C. for 30 minutes. The 'protected' thiol ester was then dissolved in dry THF (25 ml) and added to the reaction mixture, which was then stirred at 0° C. for 2h. and room temperature for 16h. under an argon atmosphere. The reaction was quenched by the dropwise addition of a saturated solution of ammonium chloride (5 ml) and the product extracted with ethyl acetate. The organic layer was washed with water, saturated brine and dried over anhydrous $MgSO_4$. The solvent was removed at reduced pressure and the residue dissolved in 1,4-dioxan/water (4:1; 5 ml). One drop of 1 N HCl was added and the solution stirred for 2½ minutes. Excess sodium bicarbonate solution was then added and the product extracted with ethyl acetate. The organic layer was washed with water, saturated brine and dried ($MgSO_4$). Removal of the solvent at reduced pressure afforded a multi-component mixture as a yellow oil (0.320 gm;).

Purification by silica gel column chromatography (Type 60; 30 g), eluting with 2% methanol/chloroform, gave the impure ketone as a pale yellow oil (0.086 g). This oil was rechromatographed over silica gel (Type 60; 4 g). Elution with 1% methanol/chloroform gave the n-butyl ketone as a colourless oil (0.030 g; 8%), $\lambda_{max}$ (EtOH) 240 nm ($\epsilon m$ 7,900); $\nu_{max}$ ($CHCl_3$) 3400, 1675, 1610 $cm^{-1}$; $\delta_H$ ($CHCl_3$) 6.20 (1H, s, CH=C); 2.44 (2H, t, $COCH_2$); 1.99 (3H, s, $CH_3$-15); 1.19 (3H) (d, J=6.0 Hz, $CH_3$-14); 0.9 (6H) (d+t, $CH_3$-17+(−$CH_2$−$)_3CH_3$); $\delta_c$ ($CDCl_3$) 203.9, 157.5, 125.8, 76.6, 71.3, 70.2, 67.6, 65.7, 61.4, 56.0, 44.0, 43.0, 39.0, 36.2, 31.9, 27.4, 26.4, 20.7, 13.8, 12.7, m/e (ammonia C.I,) 402 (20; M+$NH_4^+$), 367 (40), 349 (10), m/e 384.2489 $M^+$, 1%, $C_{21}H_{36}O_6$ requires 384.2466), 366 (5), 348 (2), 309 (2), 291 (2), 227 (40), 85 (100%), 57 (75).

EXAMPLE 5

1-[3R,4R-Dihydroxy-5S-(2S,3S-epoxy-5S-hydroxy-4S-methylhexyl]tetrahydropyran-2S-yl]-2-methyloct-2E-en-4-one (i) Butyl manganous chloride Under nitrogen, anhydrous manganous chloride (1.51 g, 12 mM) and anhydrous lithium chloride (1.02 g, 24 mM) were stirred in dry THF (25 ml). When a pale yellow, cloudy solution was obtained, the solution was cooled to 0° C. and butyl lithium (1.6 M in hexane, 11.3 ml, 18 mM was added dropwise. The reaction was then stirred at room temperature for ½ hour, giving a black solution.

(ii) Mixed anhydride

Isobutyl chloroformate (0.43 ml, 3 mM) was added to a solution of monic acid A (1.032 g, 3 mM) and triethylamine (0.42 ml, 3 mM) in THF (25 ml) at −10° C. After stirring at room temperature for ½ hour, the reaction was filtered and the filtrate treated with bistrimethylsilylacetamide (2.5 ml, excess). The solution was stirred overnight at room temperature then evaporated to dryness in vacuo, and dried at 50° C./0.5 mm for ½ hour.

(iii) α, β-Unsaturated ketone

The mixed anhydride was dissolved in dry THF (25 ml) and treated at −20° C. under nitrogen with butyl manganous chloride then stirred over the weekend at room temperature. The reaction was then poured into saturated aqueous ammonium chloride and extracted with ethyl acetate. The combined extracts were washed with aqueous sodium bicarbonate and brine then dried ($MgSO_4$) and evaporated in vacuo. The product was dissolved in 1,4-dioxan:water (4:1, 20 ml) and shaken with 10 M hydrochloric acid (5 drops) for 10 minutes when excess aqueous sodium bicarbonate solution was added. The solution was extracted with ethyl acetate and the combined extracts washed with brine and dried ($MgSO_4$). Removal of the solvents in vacuo afforded an oil which was chromatographed twice on silica (10 g) eluting with 0–4% methanol in chloroform. Fractions containing pure product were combined and evaporated to yield (88 mg, 8%) spectroscopically and chromatographically identical material to that obtained in Example 3.

EXAMPLE 6

1-[3R,4R-Dihydroxy-5S-(2S,3S-epoxy-5S-hydroxy-4S-methylhexyl)tetrahydropyran-2S-yl]-2-methyloct-2E-en-4-one (i) Butyl manganous chloride Manganous chloride (7.55 g, 60 mM) and lithium chloride (5.1 g, 120 mM) were stirred under nitrogen in dry THF (150 ml) until a cloudy yellow solution was obtained. The complex was cooled to −20° C. and butyl lithium (1.6 M in hexane, 45 ml, 72 mM) added dropwise and the reaction stirred at 0° C. for ¾ hour.

(ii) Mixed anhydride

Isobutyl chloroformate (2.14 ml. 15 mM) was added to a solution of monic acid A (5.16 g, 15 mM) and triethylamine (2.1 ml, 15 mM) at −20° C. in THF (50 ml). The solution was stirred at 0° C. for 1 hour then filtered and triethylamine (6.9 ml) added, followed by dropwise addition of trimethylsilyl chloride (6.3 ml) at −20° C. The reaction was stirred overnight at room temperature then filtered and evaporated in vacuo and redissolved in ethyl acetate. After washing with sodium bicarbonate and brine, the solution was dried ($MgSO_4$) and evaporated to an oil.

(iii) α,β-Unsaturated ketone

The mixed anhydride in THF (100 ml) was added dropwise to the butyl manganous chloride solution under nitrogen at 0° C. and stirred at ambient temperatures for 1 hour. The reaction mixture was then poured into saturated aqueous ammonium chloride and extracted with ethyl acetate. The combined extracts were washed with sodium bicarbonate and brine, then dried ($MgSO_4$) and evaporated in vacuo. The product was dissolved in 1,4-dioxan/water (4:1, 80 ml) and shaken with 10 M hydrochloric acid (20 drops) for 10 minutes when excess sodium bicarbonate was added. The solution was extracted with ethyl acetate and the combined extracts washed with brine and dried ($MgSO_4$). Removal of the solvents in vacuo afforded an oil which was chromatographed on silica (50 g) eluting with 0–4% methanol in chloroform. Fractions containing pure product were combined to yield desired α,β-unsaturated butyl ketone (1.27 g, 22%), identical to the material obtained in Example 3. Impure fractions were combined and rechromatographed to yield a further (0.2 g, 3%). A second component was also isolated and identified as 1-[3R,4R-dihydroxy-5S-)2S,3S-epoxy-5S-hydroxy-4S-methylhexyl)tetrahydropyran-2S-yl]-2-methyl-oct-2Z-en-4-one (1.0 g, 17%) identical to the material obtained in Example 4.

EXAMPLE 7

1-[3R,4R-Dihydroxy-5S-(2S,3S-epoxy-5S-hydroxy-4S-methylhexyl)tetrahydropyran-2S-yl]-2-methyloct-2E-en-4-one (i) Butyl manganous chloride Under argon, butyl lithium (1.6 M in hexane, 54 ml, 86 mM) was added to a suspension of manganous chloride (7.55 g, 60 mM) in dry THF (125 ml) at −10° C. and the dark solution stirred for a further ¾ hour at room temperature.

(ii) Mixed anhydride

Isobutyl chloroformate (2.05 ml, 15.8 mM) was added to a solution of monic acid A (5.16 g, 15 mM) and triethylamine (2.3 ml, 16.5 mM) in THF (100 ml) at −20° C. The reaction was stirred at room temperature for a further ½ hour, then filtered.

(iii) α,β-Unsaturated ketone

The mixed anhydride solution was added under argon to the butyl manganous chloride solution at −20° C. After stirring for 1½ hours at room temperature, the reaction mixture was poured into saturated ammonium chloride solution. The product was extracted with ethyl acetate and the combined extracts washed with saturated sodium bicarbonate and brine, then dried ($MgSO_4$). Evaporation of the solvent in vacuo followed by chromatography on silica (40 g) eluting with 0-8% methanol in dichloromethane gave 350 mg (6%) of the α,β-unsaturated butyl ketone, identical to the material obtained in Example 3.

EXAMPLE 8

4-{5-[5-(2,3-Epoxy-5-hydroxy-4-methylhexyl)-3,4-dihydroxytetrahydropyran-2-yl]-4-methylpent-3E-en-2-onyl}pyridine (i) Mixed anhydride Isobutyl chloroformate (0.39 ml) was added to a solution of monic acid A (1.03 g) and triethylamine (0.46 ml) in THF (25 ml) at 0° C. After stirring for 1 hr at room temperature, the solution was cooled to 0° C. and triethylamine (1.38 ml) and trimethylsilyl chloride (1.26 ml) were added. The reaction was stirred for 3 hr at room temperature then filtered and evaporated in vacuo.

(ii) 4-Pyridylmethylmanganous chloride

Under argon, butyl lithium in hexane (4.1 ml, 1.6 M solution) was added to a solution of 4-picoline (0.58 ml) in THF (25 ml) at −30° C. The solution was stirred for 1 hr at room temperature then cooled to 0° C. and anhydrous manganese chloride (0.76 g) added. The reaction was then stirred at room temperature for 1 hr.

(iii) α,β-Unsaturated ketone

The protected mixed anhydride in THF (20 ml) was added under argon to the 4-pyridylmethyl manganous chloride solution at 0° C. then stirred at room temperature for 2 hr. After pouring onto saturated aqueous ammonium chloride the product was extracted with ethyl acetate and the combined extracts were washed with sodium bicarbonate then brine. The solution was dried ($Na_2SO_4$) and evaporated to an oil which was redissolved in 1,4-dioxan/water (20 ml) and treated with 10 M-hydrochloric acid (5 drops). After 5 min excess sodium bicarbonate was added and the solution extracted with ethyl acetate. The combined extracts were washed with brine then dried ($Na_2SO_4$) and evaporated in vacuo. Chromatography on silica (10 g) eluting with 0 to 9% methanol in methylene chloride gave the product, which was rechromatographed on silica (4 g) to give pure ketone (40 mg, 3%) $\nu_{max}$ ($CHCl_3$) 3370 (broad), 1680, 1615 and 1600 cm$^{-1}$; $\lambda_{max}$ (EtOH) 245 nm ($\epsilon_m$ 6,666); $\delta_H$ ($CDCl_3$) 0.91 (3H, d, $CH_3$-17), 1.18 (3H, d, $CH_3$-14), 1.15 (3H, s, $CH_3$-15), 3.68 (2H, s, $CH_2$), 6.20 (1H, s, H-2), 7.22 (2H, m, CH-3'), 8.51 (2H, m, CH-2').

EXAMPLE 9

4-{5-[5-(2,3-Epoxy-5-hydroxy-4-methylhexyl)-3,4-dihydroxytetrahydropyran-2-yl]-4-methylpent-3E-en-2-onyl}pyridine (i) Mixed anhydride Isobutyl chloroformate (0.39 ml) was added to a solution of monic acid A (1.03 g) and triethylamine (0.46 ml) in THF (25 ml) at 0° C. After stirring for 1 hr at room temperature the reaction mixture was filtered and evaporated in vacuo.

(ii) 4-Pyridylmethylmanganous chloride

Under argon, butyl lithium in hexane (8.35 ml, 1.6 M solution) was added to a solution of 4-picoline (1.23 g) in THF (25 ml) at −30° C. slowly over 20 mins. The solution was then stirred at room temperature for 1 hr and anhydrous manganous chloride (1.51 g) added at 0° C. The suspension was stirred for ca. ¾ hr at room temperature.

(iii) α,β-Unsaturated ketone

A solution of the mixed anhydride (20 ml) was added to the 4-pyridylmethylmanganous chloride solution under argon at 0° C. The reaction was stirred for 2½ hr at room temperature then poured onto saturated aqueous ammonium chloride. The product was extracted with ethyl acetate and the combined extracts were combined and washed with sodium bicarbonate and brine then dried ($MgSO_4$). After evaporation to an oil the product was chromatographed on silica (10 g then 4 g) eluting with 0 to 9% methanol in methylene chloride to yield 4-pyridylmethyl ketone (40 mg, 3%) identical to the material obtained in Example 8.

BIOLOGICAL DATA (a) Human Bacteria

Table 1 shows the MIC values (μg/ml) of the compounds of Examples 1 to 3 against a number of organisms important in human infections obtained by serial dilution in nutrient agar containing 5% "chocolated" horse blood.

TABLE 1

| ORGANISM | Compound of Example No. | | |
|---|---|---|---|
| | 1 | 2 | 3 |
| E. coli NCTC 10418 | >100 | >50 | >100 |
| E. coli ESS | 10 | — | 1.0 |
| P. mirabilis 889 | 50 | >50 | 100 |
| K. aerogenes A | >100 | >50 | >100 |
| Ps. aeruginosa 10662 | >100 | >50 | >100 |
| Pasteurella multocida 1633 | 5.0 | 2.5 | 0.5 |
| Haemophilus influenzae Q1 | 0.5 | 0.2 | 0.2 |
| Haemophilus influenzae Wy21 | 1.0 | 0.5 | 0.2 |
| Neisseria catarrhalis 1502 | 0.2 | 0.5 | 0.5 |
| Bacillus subtilis 6633 | 5.0 | 2.5 | 0.5 |
| Corynebacterium xerosis 9755 | >100 | 25.0 | 100 |
| Sarcina lutea 8340 | >100 | >50 | >100 |
| Staph. aureus Oxford | 1.0 | 1.2 | 1.0 |
| Staph. aureus Russell | 5.0 | 2.5 | 1.0 |
| Staph. aureus W2827 | >100 | 2.5 | 2.5 |
| Strep. faecalis | >100 | >50 | >100 |
| Strep. pyogenes A 64/848 | 50 | 12.5 | |
| Strep. pyogenes B 2788 | 50 | 25.0 | 2.5 |
| Strep. pyogenes C 2761 | 100 | 25.0 | 2.5 |
| Strep. pneumoniae CN33 | 25 | 12.5 | 5.0 |

(b) Veterinary Bacteria

Table 2 shows the MIC values (µg/ml) of the compounds of the Examples against a number of organisms important in veterinary infections.

The MIC values were determined by agar dilution using diagnostic sensitivity test agar (Oxoid) using a multipoint inoculator delivering 0.001 ml of an inoculum adjusted to give $10^7$–$10^8$ organisms per ml and read after 24 hours incubation at 37° C.

TABLE 2

| Organism | Compound of Example No | | |
|---|---|---|---|
|  | 1 | 2 | 3 |
| E. coli NCTC 10418 | >80 | >40 | >80 |
| E. coli E1 | >80 | >40 | >80 |
| S. dublin S7 | >80 | >40 | >80 |
| S. typhimurium S18 | >80 | >40 | >80 |
| Bord. bronchiseptica B08 | >80 | >40 | >80 |
| Bord. bronchiseptica B09 | 20 | 40 | 40 |
| Past. multocida PA1 | 5 | 0.625 | 2.5 |
| Past. multocida PA2 | 5 | 0.312 | 1.25 |
| Past. haemolytica PA5 | 10 | 5 | 20 |
| Erysipelothrix rhusiopathiae NCTC 8163 | >80 | >40 | >80 |
| Corynebacterium pyogenes CY1 | >80 | >40 | >80 |
| Staph. aureus B4 (pen resis) | 10 | .625 | 2.5 |
| Staph. aureus 152 (pen sens) | 10 | 0.312 | 2.5 |
| Staph. aureus Oxford |  | 0.312 | 2.5 |
| Strep. suis (group D) SPS11 | >80 | >40 | >80 |
| Strep. uberis SPU1 | 20 | 5 | 2.5 |
| Strep. dysgalactiae SPD1 | 80 | 20 | 10 |
| Strep. agalactiae SPA1 | >80 | 20 | 10 |

(c) Anti-Mycoplasma Activity

Table 3 shows the in vitro MIC values (µg/ml) of the compounds of Examples 1 to 3 against a number of mycoplasma organisms. The MIC values were determined by serial dilution in Friis modified agarose medium.

TABLE 3

| ORGANISM | Compound of Example No. | | |
|---|---|---|---|
|  | 1 | 2 | 3 |
| M. suipneumoniae NB12 | >10 | 2.5 | 1.0 |
| M. suipneumoniae JF 435 | 10 | 5.0 | 1.0 |
| M. siupneumoniae HK(2) | >10 | 2.5 | 1.0 |
| M. suipneumoniae Str. 11 | 5 | 2.5 | 0.5 |
| M. suipneumoniae J2206/183b | >10 | 5.0 | 1.0 |
| M. suipneumoniae MS 16 | 10 | 2.5 | 0.5 |
| M. suipneumoniae PW/C/210 | 10 | 2.5 | 0.5 |
| M. suipneumoniae LABER | 5 | 2.5 | 0.5 |
| M. suipneumoniae UCD 1 | >10 | 5.0 | 1.0 |
| M. suipneumoniae TAM 6N | >10 | 2.5 | 1.0 |
| M. suipneumoniae ATCC 25095 | 10 | 2.5 | 1.0 |
| M. suipneumoniae NCTC 10110 | >10 | 5.0 | 1.0 |
| M. hyorhinis ATCC 23234 | 10 | 2.5 | 0.5 |
| M. hyorhinis ATCC 25021 | 10 | 2.5 | 0.5 |
| M. hyosnoviae ATCC 25591 | 5 | 2.5 | 0.25 |
| M. bovis NCTC 10131 | 0.25 | 0.1 | 0.025 |
| M. bovigenitalium ATCC 14173 | 0.5 | 0.1 | 0.05 |
| M. dispar NCTC 10125 | 2.5 | 0.5 | 0.25 |
| M. gallisepticum S6 | >10 | >10 | >10 |
| M. pneumoniae ATCC 15492 | >10 | >10 | 10 |

Serum Binding

Serum binding was assessed by ultrafiltration of procine serum containing compounds at 8 mcg/ml, and through an Amicon CF50A ultrafiltration cone. Separation of ultrafiltrate was achieved by centrifugation. Unbound concentrations of compound were measured in the ultrafiltrate by microbiological assay (B. subtilis ATCC 6633) against standards prepared in saline.

| EXample No. | % Bound to Pig Serum |
|---|---|
| 1 | 14.8 |
| 2 | 26.1 |
| 3 | 53.1 |

Mouse blood levels of Example 1 following its oral and subcutaneous administration Blood levels were assessed in albino male mice (18–22 g CSI). The dose was 50 mg/kg administered in a 10% DMF solution orally and subcutaneously. The mice were killed at intervals up to 4 hours and the blood assayed microbiologically using B. subtilis.

| Example | Route of Administration | Conc. µg/ml at mins after dosing | | | | | | |
|---|---|---|---|---|---|---|---|---|
|  |  | 5 | 10 | 20 | 30 | 60 | 120 | 240 |
| 1 | Subcutaneous | 16.4 | 15.3 | 9.8 | 5.0 | <3.0 | <3.0 | <3.0 |
| 1 | Oral | 5.9 | 7.7 | 4.8 | <3.0 | <3.0 | <3.0 | <3.0 |

Mouse blood levels of Example 3 following its oral and subcutaneous administration Blood levels were assessed in albino male mice (strain OLAC: MF-1, 18–22 g). The dose was 50 mg/kg administered in a 10% ethanol solution orally and subcutaneously. The mice were killed at intervals up to 90 min and the blood assayed microbiologically using B. subtilis ATCC 6633 in TSA at pH 8.0.

| Ex. | Route of administration | Conc. (µg/ml) at min after dosing | | | | | | |
|---|---|---|---|---|---|---|---|---|
|  |  | 5 | 10 | 20 | 30 | 45 | 60 | 90 |
| 3 | Subcutaneous | 19.8 | 15.5 | 7.3 | 2.2 | <1.5 | <1.5 | <1.5 |
| 3 | Oral | 9.4 | 5.1 | <1.5 | <1.5 | <1.5 | <1.5 | <1.5 |

Mean serum concentrations in neonatal piglets of Example 3 after intramuscular or oral administration at 50 mg/kg Blood levels were assessed in neonatal piglets (mean bodyweight ca. 3 kg). The dose was 50 mg/kg administered as a 25 mg/ml of 25% aqueous ethanol solution. Doses were given by intramuscular injection and orally by stomach tube. Piglets were bled at intervals up to 24 hr and the serum assayed microbiologically using B. subtilis ATCC 6633.

| Example | Route of administration | Serum concentration (µg/ml) at: | | | | | | |
|---|---|---|---|---|---|---|---|---|
|  |  | 10' | 20' | 40' | 60' | 2hr | 3hr | 4hr |
| 3 | i.m. | 8.5 | 7.9 | 5.1 | 4.3 | 1.3 | 1.2 | <0.07 |
| 3 | p.o. | 3.1 | 2.0 | 1.4 | 0.83 | 0.70 | 0.60 | <0.07 |

Mean serum concentrations in milk weaned piglets of Example 3 after oral administration at 50 mg/kg Blood levels were assessed in milk weaned piglets (mean bodyweight 4.1 kg). The dose was 50 mg/kg administered orally (intubation) as a 25 mg/ml of 25% aqueous ethanol solution. Piglets were bled at intervals up to 24 and the serum assayed microbiologically using *B. subtilis* ATCC 6633.

| Example | Route of administration | Serum concentration (μg/ml) at: | | | | | | | | |
|---|---|---|---|---|---|---|---|---|---|---|
| | | 10' | 20' | 40' | 60' | 2 hr | 3 hr | 4 hr | 6 hr | 8 hr |
| 3 | p.o. | 2.1 | 1.9 | 0.72 | 1.1 | 0.48 | 0.37 | 0.20 | 0.11 | <0.06 |

We claim:

1. A compound of the formula (II):

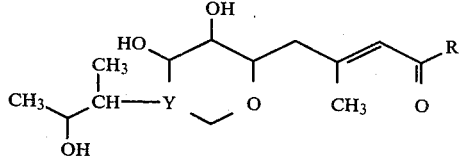

wherein Y represents

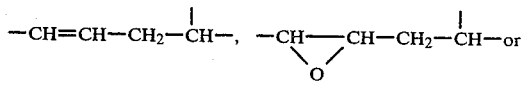 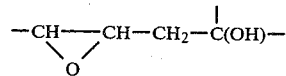

and R represents a $C_{1-10}$ alkyl, $C_{2-10}$alkenyl, $C_{2-10}$alkynyl, aryl, aralkyl or cycloalkylalkyl group, optionally substituted with halogen, $C_{1-6}$alkyl, $C_{1-6}$alkoxy, hydroxy, carboxy or $C_{1-6}$alkoxy carbonyl, or pyridyl.

2. A compound according to claim 1 in which R represents a straight or branched chain $C_{1-10}$ alkyl group.

3. A compound according to claim 2 in which R represents a straight chain $C_{1-6}$ alkyl group.

4. A compound according to claim 1 in which R represents a phenyl or benzyl group.

5. A pharmaceutical or veterinary composition comprising an antibacterially effective amount of a compound according to claim 1 together with a pharmaceutically or veterinary acceptable carrier or excipient.

6. A composition according to claim 5 in dosage unit form.

7. A composition according to claim 5 in the form of an animal foodstuff or drinking water supply.

* * * * *